US009234608B2

(12) United States Patent
Stearns et al.

(10) Patent No.: US 9,234,608 B2
(45) Date of Patent: Jan. 12, 2016

(54) HEATED ROTARY VALVE FOR CHROMOTOGRAPHY

(71) Applicant: Valco Instruments Company, L.P., Houston, TX (US)

(72) Inventors: Stanley D. Stearns, Houston, TX (US); Martin Paul Brisbin, Houston, TX (US); David Miller, Gig Harbor, WA (US)

(73) Assignee: Valco Instruments Company, L.P., Houston, TX (US)

( * ) Notice: Subject to any disclaimer, the term of this patent is extended or adjusted under 35 U.S.C. 154(b) by 223 days.

(21) Appl. No.: 14/146,596

(22) Filed: Jan. 2, 2014

(65) Prior Publication Data

US 2015/0184774 A1    Jul. 2, 2015

(51) Int. Cl.
| F16K 49/00 | (2006.01) |
| G01N 30/20 | (2006.01) |
| F16K 11/085 | (2006.01) |
| F16K 11/076 | (2006.01) |
| G01N 30/30 | (2006.01) |

(52) U.S. Cl.
CPC ............. *F16K 49/002* (2013.01); *F16K 11/076* (2013.01); *F16K 11/085* (2013.01); *G01N 30/20* (2013.01); *G01N 2030/202* (2013.01); *G01N 2030/3053* (2013.01); *Y10T 137/6416* (2015.04); *Y10T 137/6606* (2015.04)

(58) Field of Classification Search
CPC .......... G01N 30/20; G01N 2030/3046; G01N 2030/202; G01N 30/30; G01N 2030/3053; G01N 2030/3084; F16K 11/0743; F16K 11/076; F16K 11/085; F16K 49/002
USPC ....................................................... 73/23.42
See application file for complete search history.

(56) References Cited

U.S. PATENT DOCUMENTS

| 3,203,249 | A |   | 8/1965  | Jentzsch et al. |
| 4,890,502 | A |   | 1/1990  | Elias et al. |
| 4,948,389 | A | * | 8/1990  | Klein ................ G01N 30/30 95/18 |
| 5,032,151 | A | * | 7/1991  | Klein ................ G01N 30/24 95/17 |
| 5,402,668 | A | * | 4/1995  | Murakami ......... G01N 33/0016 436/161 |
| 5,889,197 | A | * | 3/1999  | van der Maas ..... G01N 30/6004 73/23.42 |
| 6,491,063 | B1 | * | 12/2002 | Benatav ............... F25B 41/046 137/625.43 |
| 6,910,394 | B2 | * | 6/2005  | Kriel ................... G01N 30/20 73/863.11 |
| 8,905,075 | B2 | * | 12/2014 | Tower .................. F16K 3/08 137/625.15 |

(Continued)

OTHER PUBLICATIONS

Blaine R. Copenheaver, International Search Report—PCT/US2014/072424, Apr. 22, 2015, 5 pages, United States Patent and Trademark Office as International Searching Authority, Alexandria, Virginia, USA.

(Continued)

*Primary Examiner* — Freddie Kirkland, III (74) *Attorney, Agent, or Firm* — Crain, Caton & James, P.C.; James E. Hudson, III (57) ABSTRACT

A heated rotary valve for use in connection with a sample to be separated in a column for heating the sample to temperature within the valve. The heated rotary valve permits introduction of compounds, having a wide boiling range, into a gas chromatograph with improved precision of area and retention time. The valve includes a stator, an elongate body, a rotor seal, a drive shaft, and an internal element for generating heat. The rotor seal may be laterally captured by a ring to prevent movement or creep due to heat absorption during operation.

21 Claims, 6 Drawing Sheets

(56) References Cited

U.S. PATENT DOCUMENTS

| | | | | |
|---|---|---|---|---|
| 9,063,114 | B2* | 6/2015 | Wiechers | G01N 30/26 |
| 2002/0178843 | A1 | 12/2002 | Kriel | |
| 2011/0006237 | A1* | 1/2011 | Tower | F16K 3/08 251/304 |

OTHER PUBLICATIONS

Blaine R. Copenheaver, Written Opinion of the International Searching Authority—PCT/US2014/072424, Apr. 22, 2015, 8 pages, United States Patent and Trademark Office as International Searching Authority, Alexandria, Virginia, USA.

Search History incident to the International Search Report—PCT/US2014/072424, Feb. 27, 2015, 3 pages, United States Patent and Trademark Office as International Searching Authority, Alexandria, Virginia, USA.

Freddie Kirkland III, International Preliminary Report on Patentability—PCT/US14/72424, Nov. 10, 2015, 3 pages, United States Patent & Trademark Office as International Preliminary Examining Authority, Alexandria, Virginia, USA.

\* cited by examiner

HEATED ROTARY VALVE FOR CHROMOTOGRAPHY

CROSS-REFERENCE TO RELATED APPLICATIONS

None.

STATEMENT REGARDING FEDERALLY SPONSORED RESEARCH OR DEVELOPMENT

Not Applicable.

BACKGROUND

1. Field

The present disclosure pertains to valves and systems for use in chromatography. More particularly, the present disclosure pertains to a heated rotary valve for use in connection with a sample to be separated in a column for heating the sample to temperature within the ports of the valve. The heated rotary valve permits introduction of a wide boiling range compounds into a gas chromatograph with improved precision of area and retention time.

2. Description of the Related Art

Gas chromatography (GC) is generally performed on a sample using a column positioned within and heated by an oven or other heating device, wherein the sample is heated before introduction to the column. The separated sample is then introduced to a detector for identification of compounds. Chromatagraphy ovens may be operated at elevated temperatures in the range of 40' C to 400' C. Because the column is typically a coil of thin tube, such as of metal or fused silica, with an internal polymer coating, the column rapidly reaches the ambient temperature within the oven or applied by an external heating element, which permits movement of the sample through the column. Problematically, the sample needs to be heated to the elevated temperature of the column. This is sometimes accomplished using a heated injection port where the sample size is sufficiently small, such that the injection can be accomplished using a syringe which peirces a septum—a thick, rubber disk. Heated injection ports are sufficiently hot that the sample boils and is carried into the column as a gas by helium or another carrier.

Historically, liquid injection for gas chromatography has included liquid injection by a syringe, whether split on column, but which, while simple, suffered from issues of septum lifetime and an automation system more complex that associated with a valve. The historic alternative was injection by valve, whether a one zone system such as standard liquid sample valves) or two zone injection systems, in which a sampe is moved from a cool zone, such as a sample supply, to a hot zone, such as the column. While more easily controlled and repeatable, these valve systems suffered the difficulty of ensuring the sample was at the temperature of the hot zone when reached.

Additionally, because of the large internal volumes of the valves known in the art, not only was heating unfeasible, but recycling of samples through columns repeatedly for high separation was largely only theoretical as those valves, typically using releatively large fitting adapters (1/16 inch or 1/32 inch, for example) introduced peak broadening in each switch, as those fittings were incompatible with small bore columns. Alternatives have included use of Dean's switching and other pressure differential methods using external solenoid valves to control the carrier gas direction. None have been highly effective for column switching.

It would be desirable to incorporate a sample which may be introduced according to a mechanically controlled system and which would be at temperature for processing through the chromatography system, but otherwise would not transfer heat or suffer from heat soak.

Additionally, in chromatography systems, it is typical that the sample may be flowed through a valve during times when no analysis is desired or ongoing. Providing a valve at an elevated temperature during those off-analyzing periods in contact with a flowing sample could be detrimental to the sample, as it could result is repeated vaporization of the sample prior to analysis.

It would therefore be desirable to provide a valve for communication with a sample source, where the valve would permit sample to flow to the column while simultaneously heating the sample to temperature for during the analysis period, but which would otherwise not introduce heat into the surrounding system or to the sample.

It would therefore be desirable to provide a valve having an internal volume of only a few nanoliters which could be used for column switching at an elevated temperature without undesirable cooling or unnecessary additional heating equipment.

SUMMARY

The present disclosure therefore meets the above needs and overcomes one or more deficiencies in the prior art by providing a heated rotary valve for use in connection with one or more heated columns so that a sample, heated to, or maintained at, temperature in the valve may then be separated in a column heated to the same temperature.

The present disclosure provides a heated rotary valve which includes a stator, an elongate body, a rotor seal, a drive shaft and an element for generating heat. The stator has a stator first surface and a stator second surface, where the stator first surface has a plurality of stator connectors while the stator second surface includes a flat plate. The stator has a plurality of stator ports, each extending from a connector to the flat plate of the stator second surface.

The elongate body has an internal bore from a body first end to a body second end in which a drive shaft is positioned so as to free rotate. The stator is affixed at its second surface to the body at the body first end, so as to form an integral unit in which the rotor seal may be rotated. The rotor seal is a polymeric disk that makes a high pressure seal against the stator and therefore has a rotor seal first surface which is positioned adjacent the stator second surface. The rotor seal has at least one channel in its first surface to connect two stator ports when desired. The drive shaft, which extends beyond the second end of the body, is affixed to the rotor seal so that an actuator may switch the valve to connect particular parts when desired. The element for generating heat is affixed to the body in or at the body first end proximate the rotor seal's first surface and the stator's second surface, or in the stator head so that heat is transmitted to stator ports by the body, and/or the stator, which are composed of a material to transmit heat from said element for generating heat to said stator ports.

In an alternative embodiment, the valve is part of a rotary valve system which further incorporates a controller which is adapted to receive a start instruction and to activate the element for generating heat upon receipt of that start instruction.

In a further embodiment, the rotary valve system may be incorporated into a chromatography system wherein the controller is further adapted to receive an oven temperature from a temperature sensor in the oven so that the valve may be heated by the element for generating heat to the oven temperature, together with a chromatography column, a sample supply, an oven, and a temperature sensor. In the chromotography system, the valve is in communication with the chromatography column at a column inlet and with a sample supply at a supply outlet. The column, the sample supply and the temperature sensor are positioned within the oven, while the valve is positioned through the oven wall, so that the rear of the oven-side body section contact the oven wall while the oven-external body section is positioned external the oven.

Additional aspects, advantages, and embodiments of the disclosure will become apparent to those skilled in the art from the following description of the various embodiments and related drawings.

BRIEF DESCRIPTION OF THE DRAWINGS

So that the manner in which the described features, advantages, and objects of the disclosure, as well as others which will become apparent are attained and can be understood in detail; more particular description of the disclosure briefly summarized above may be had by referring to the embodiments thereof that are illustrated in the drawings, which drawings form a part of this specification. It is to be noted, however, that the appended drawings illustrate only typical preferred embodiments of the disclosure and are therefore not to be considered limiting of its scope as the disclosure may admit to other equally effective embodiments.

In the drawings.

DESCRIPTION OF THE PREFERRED EMBODIMENT

Referring to FIGS. 1-7, a heated rotary valve 100 is provided for use in connection with a sample to be separated in a column 704, heated by an oven 712 or other heating systems, for heating the sample within the ports of the valve to the temperature of the column during periods of analysis, but not otherwise heating the sample. The valve 100 may be placed so that the first surface 104 and stator connectors 108 of the stator 102 are exposed in a chromatography oven 712 in communication with a sample source 708, so that a sample to be introduced to the column 704 is heated within the valve 100 body first end 100 to the temperature of the associated chromatography column 704, but which otherwise does not introduce excess heat into the surroundings of the valve 100. Referring to FIG. 8, the heated rotary valve 100 may be positioned adjacent a column 804 which is heated by direct or indirect heat transfer, such as by a heating element bound to the column 804. The valve 100 includes a stator 102, an elongate body 112, a rotor seal 230, a drive shaft 134, all of which may be composed of stainless steel, and a element for generating heat 236, internal or external to the body 112 of the valve 100.

Figure 7:
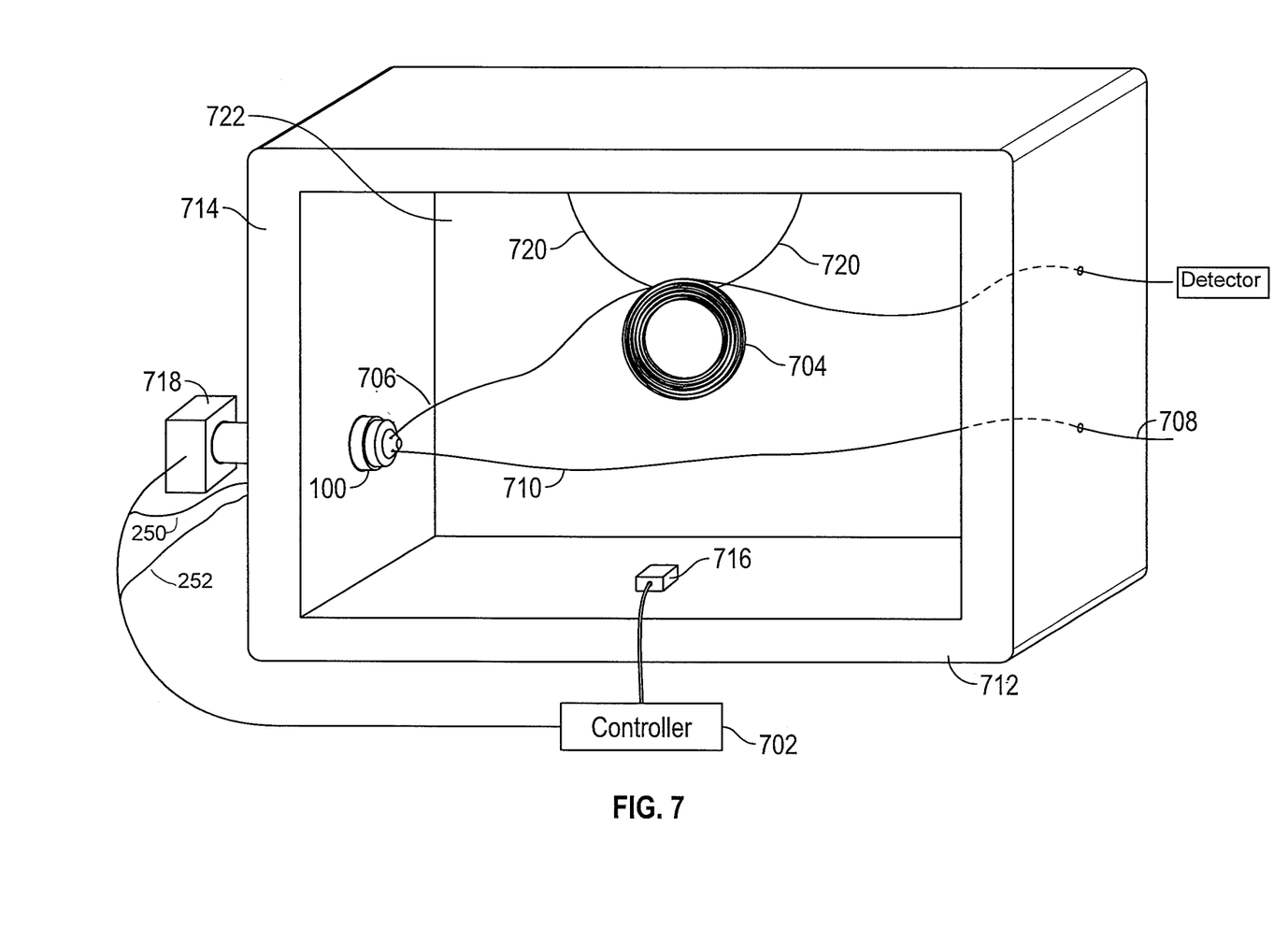
FIG. 7 is an illustration of a further embodiment of the present disclosure illustrating a heated rotary valve system and a chromatography system in an oven.
Figure 8:
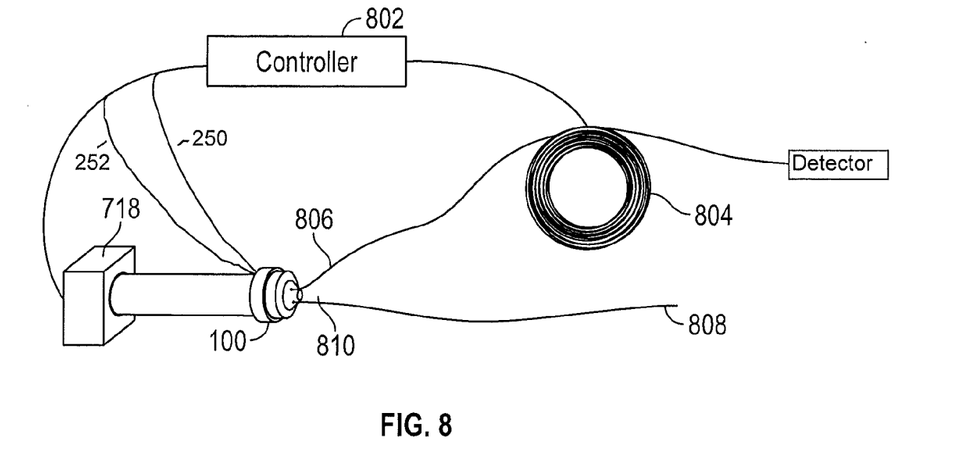
FIG. 8 is an illustration of a further embodiment of the present disclosure illustrating a heated rotary valve system and a heated column system.

Referring to FIG. 7, the stator 102 is made integral to the elongate body 112 and provides the point of connection for the valve 100 to the sample supply 708 and the column 704. Referring to FIGS. 1-6, the stator 102 has a stator first surface 104 and a stator second surface 106. The stator first surface 104 has a plurality of stator connectors 108 which provide the point of communication with the sample supply 708 and the column 704. The stator second surface 106 includes a flat plate 502 which provides a portion of the flow path for the sample in operation of the valve 100. The stator 102 has a plurality of stator ports 210, each extending from a connector 108 to the flat plate 502 of the stator second surface 106. Preferably each stator port 210 is constructed for use with 360 micrometer fittings, which reduces the volume of sample in the stator 102, and therefore further increases the heat transfer rate from the stator 102.

Figure 1:
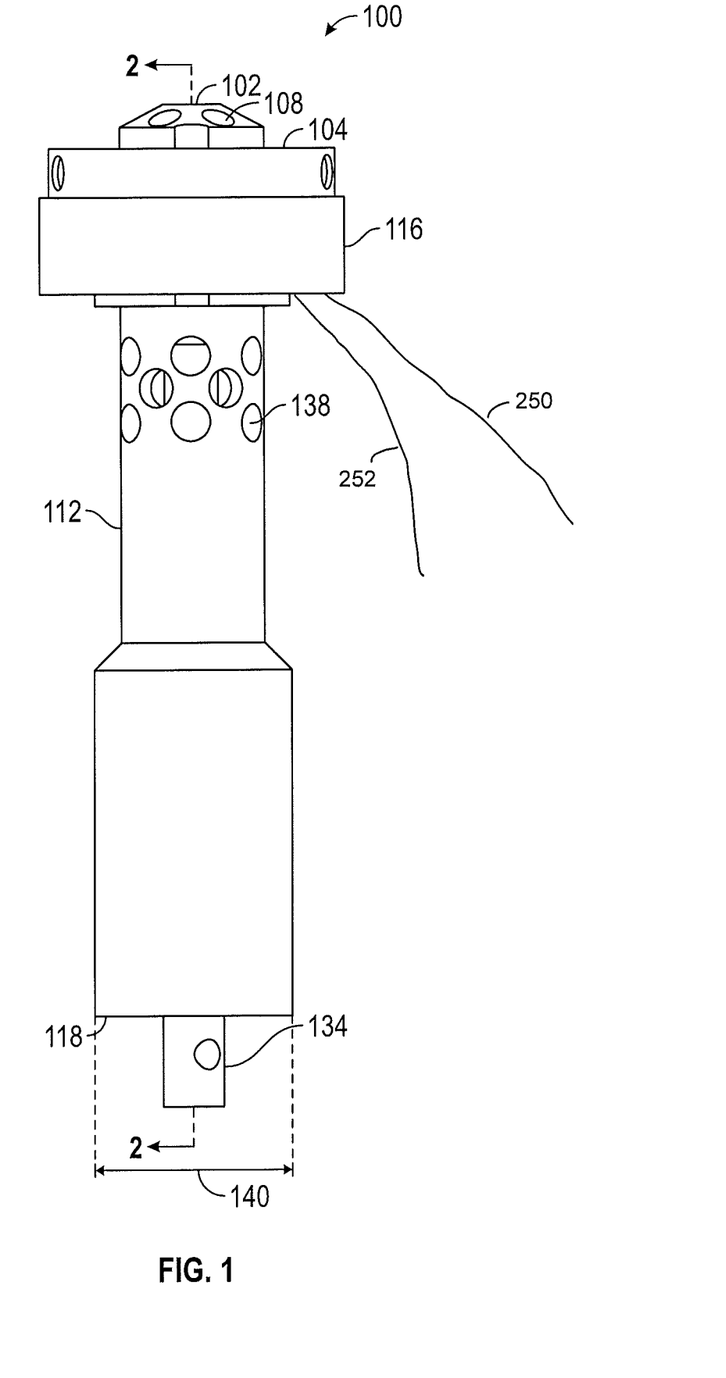
FIG. 1 is an illustration of one embodiment of the valve of the present disclosure as assembled.
Figure 2:
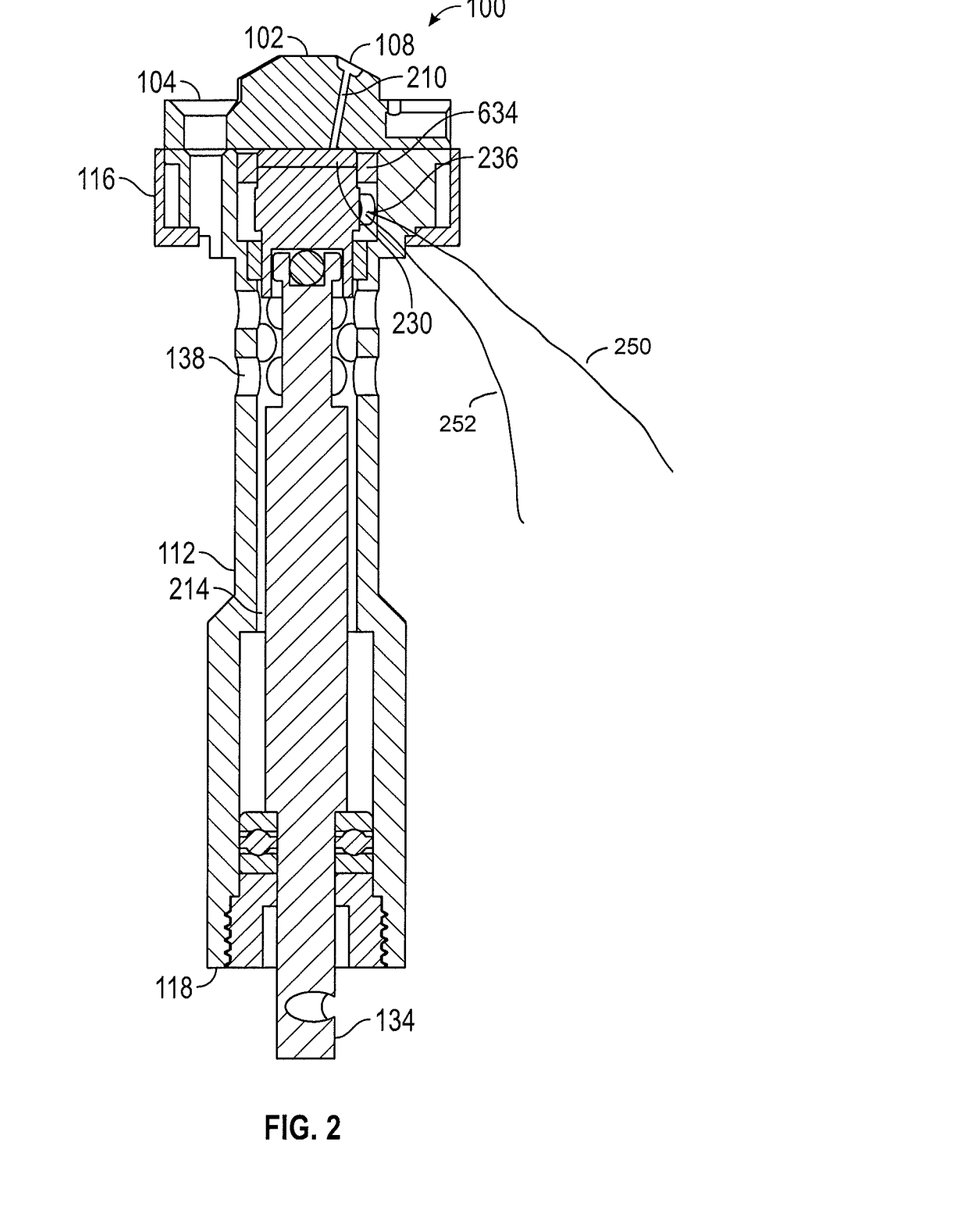
FIG. 2 is an illustration of a cross-sectional view of the embodiment FIG. 1 along line B-B of the valve of the present disclosure as assembled.
Figures 5, 6:
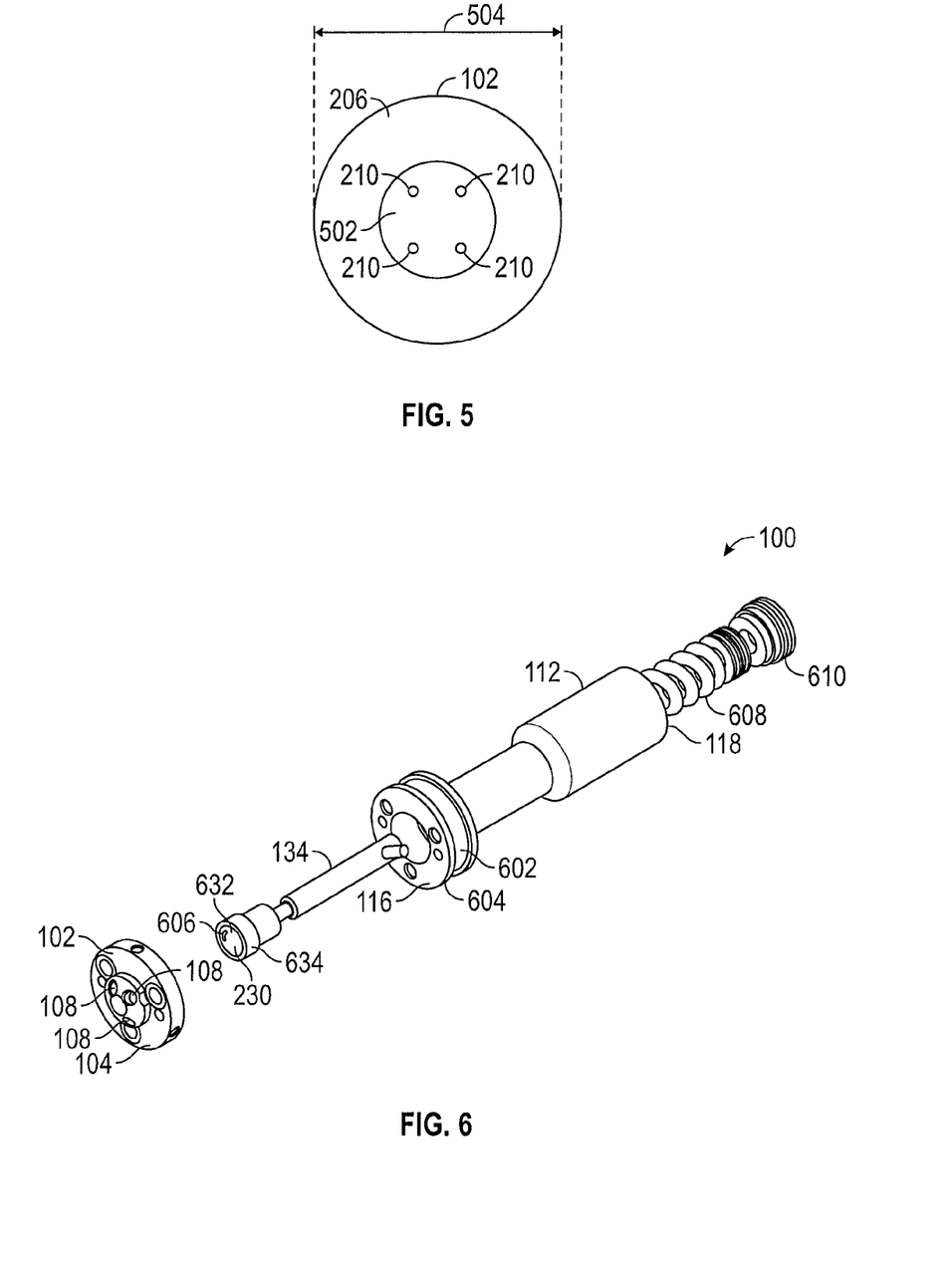
FIG. 5 is an illustration of the face of the rotor seal of the valve of the present disclosure.
FIG. 6 is an exploded view of an alternative embodiment of the present disclosure.

Referring to FIGS. 1-7, the elongate body 112 has sections intended to permit heat transfer to the stator, but not to the second end 118 wherein the drive shaft 134 is connected to an actuator 718, which permits control of the valve 100 and control over the flowpaths used. Referring to FIGS. 2 and 6, the body 112 has an internal bore 214 which extends from the body first end 116 to the body second end 118. The drive shaft 134 is positioned within the internal bore 214 of the elongate body 112 so as to freely rotate when activated by the actuator 718. Heating is desirable only in the body first end 116.

Referring to FIGS. 1-6, the stator 102 is therefore affixed at the stator second surface 106 to the body 112 at the body first end 116. As it is desirable that the stator 102 heat rapidly, while it is desirable the body 112 not retain any conducted heat, the body 112 is sized to be smaller in diameter than the stator 102 such that heat will not readily be conducted toward the body second end 118 and any conducted heat will be readily shed. The elongate body 112 may therefore have a body diameter 140 which is less than seventy-five percent (75%) of the stator diameter 504 of the stator 102.

Referring to FIGS. 2 and 6, the rotor seal 230 completes the flow path through the valve 100 depending on its position. The rotor seal 230 has a rotor seal first surface 232, which when the valve 100 is assembled, is adjacent the stator second surface 106. The rotor seal 230 has at least one channel 606 on or in the rotor seal first surface 232 which provides, when positioned, the connection of two of the stator ports 210. Referring to FIG. 7, the rotor seal 230 may be positioned to permit flow of a sample from the sample supply 708 through the valve 100 and to the column 704, or may be positioned to preclude such flow, may be positioned to cause the sample to enter a loop, or may be positioned for other desired flowpaths. Referring to FIG. 6, the rotor seal 230 is maintained in contact with the stator second surface 106 by driving the drive shaft 134 forward, such as by use of a spring 608 and end cap 610 in conjunction with the body 112.

As the heat into the valve 100 from the element for generating heat 236 may also be conducted to the rotor seal 230, a rotor ring 634 may be provided about the rotor seal 230 to contain the rotor seal 230 and prevent movement, such as creep, during heating. This is particularly true for seals provided of polymeric material, which may become more pliable, and more likely to move, when heated.

Referring to FIGS. 2 and 6, the drive shaft 134 is affixed to, or may be formed integral with the rotor seal 230. Referring to FIGS. 1-7, the drive shaft 134 extends from the rotor seal 230 to beyond the body second end 118 so that an actuator 718 may be affixed thereto which may control the position of the rotor seal 230 and therefore the flowpath through the valve 100.

Referring to FIGS. 2 and 6, the valve 100 includes an element for generating heat 236 which may be affixed, internally or externally, to the body 112 at the body first end 116 proximate the rotor seal first surface 232 and the stator second surface 206 or may be affixed, internally or externally, to the stator 102. Referring to FIG. 6, the element for generating heat 236 may be positioned in an external groove 602 about a body first end side surface 604. The element for generating heat 236 may be any of several heating elements known in the art, whether chemically or electrical, but whose temperature is controllable externally. Thus, in one embodiment, the element for generating heat 236 is an electrically-driven heating element with leads 250, 252 for connection to provide electrical energy to the element for generating heat 236, which becomes hotter due to application of electricity and which may be temperature controlled, such as by measurement of power, current, voltage and/or resistance, or which may include a thermocouple, thermistor, resistance temperature detector (RTD), or other temperature detecting device. The element for generating heat 236 may be connected to a power supply for provision of electrical energy, which may be incorporated into a controller or which may be external to the controller.

The small sizes of the components associated with chromatography ensure low mass and therefore high heat transfer rates. Maintaining the size only as necessary to permit operation minimizes mass. In particular, the stator connectors 108 and associated stator ports 210 and the rotor seal channels 606 are sized for 360 micrometer fittings. The resulting low mass may be heated directly, even by an air bath oven. As a result, the internal volume of the valve 100 is also ultra low, which speeds the heat transfer to the sample while the sample passes through the stator 102. As a result, the valve 100 may have a high maximum operating temperature, such as around 400 degrees Celcius and, because the small rotary distances, may provide fast switching between positions, such as around 125, or 250, milliseconds. Moreover, the low mass of the valve 100 provides for heating at 200 degress Celcius per minute and also provides for rapid cooling. As result, there is minimum sample vaporization during injection and low carry over. Additionally, this may provide for a sample size of a few nanoliters, up to 40 nanoliters, and beyond.

The relative small size and mass, and associated rapid heating and switching, of the valve 100 provide an improved choice for liquid injection in gas chromatography. The ease of operation of the valve 100 eliminates the issue associated with syringe injection while providing an improve valve injection.

When activated, such as a by a start signal in connection with sample introduction to a column 704, 804, the element for generating heat 236 provides heat to the valve 100, whether the stator 102, the drive shaft 134, or the body 112, which is composed of a material to transmit heat from the element for generating heat 236, to the stator ports 210, such as metal, such as stainless steel. Thus, the element for generating heat 236 is used to indirectly heat the stator ports 210, though other components are directly heated to provide the heat transfer to the stator ports 210, and therefore to the sample flowing through the stator port 210, which are sufficient small to ensure rapid heat transfer to the sample. In operation, the element for generating heat 236 is activated when needed to heat a sample, which quickly vaporizes the sample at the temperature of the column 704. When not needed, particularly when no analysis is on-going, the element for generating heat 236 is deactivated and the valve 100 begins to cool, to the ambient temperature of the oven 712 in the case of the body first end 116.

Figure 3:
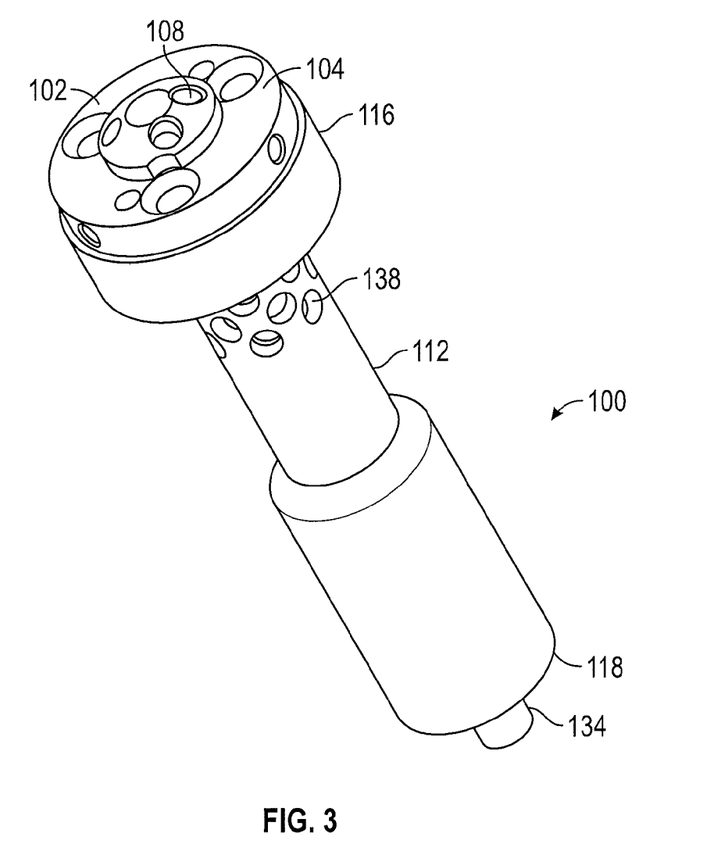
FIG. 3 is an illustration of an isometric view of the embodiment of the valve of the present disclosure.
Figure 4:
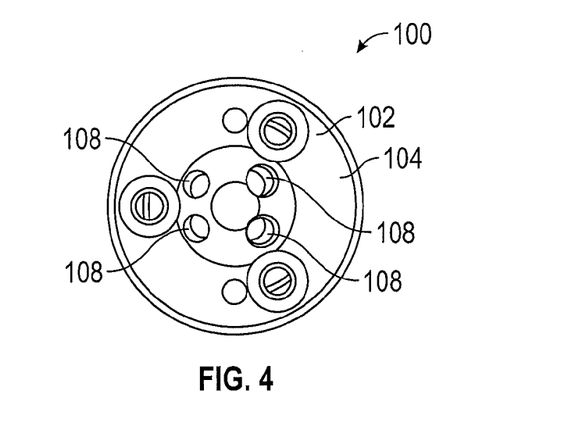
FIG. 4 is an illustration of the outer surface of the stator of the valve of the present disclosure.

Referring to FIGS. 1-3, to reduce the heat soak through the body 112, the body 112 may include a plurality of lateral vents 138 radially through the body 112 from the internal bore 214 distant the stator 102.

Referring to FIG. 7, the valve 100 may be integrated into a heated rotary valve system together with a controller 702. The controller 702 may adapted to receive a start instruction, such as when analysis using the column 704 is to be permited, to simultaneously activate the element for generating heat 236 and to cause the valve actuator 718 to position the valve 100 to permit the flow to the column 704.

Referring to FIG. 7, the heated valve system may be coupled with an improved controller 702, a chromatography column 704, which may be connected to a detector, a sample supply 708, and oven 712, and a temperature sensor 716 to provide a chromotagraphy system. In the chromotagraphy system, the controller 702 may further be adapted to receive an oven temperature from a temperature sensor 716 in the oven 712. The chromography column 704, also positioned in the oven 712, such as by suspension lines 720, is attached for communication with the valve 100 at a column inlet 706 while the sample supply 708, which may also be in the oven 712, is attached for communication with the valve 100 at a supply outlet 710. The valve 100 may be positioned through the oven wall 714, so that only the stator first surface 104 and stator connectors 108 are exposed to the interior 722 of the oven 712, while the body second end 118 and the end of the driveshaft 134 are sufficient external the oven wall 714 to permit connection with the valve actuator 718.

Referring to FIG. 8, the heated valve 100 may be coupled with an improved controller 802, a chromatography column 804, which may be connected to a detector, and a sample supply 808 to provide an alternative chromotagraphy system. In the alternative chromotagraphy system, the controller 802 may further be adapted to control the temperature of a column 804 which may be heated by direct contact, or indirect contact, with a heating element. The chromography column 804 is attached for communication with the valve 100 at a column inlet 806 while the sample supply 808 is attached for communication with the valve 100 at a supply outlet 810. Thus, the valve 100 and column 804 may be adapted for a portable chromatography system.

The construction of the valve 100 permits rapid column switching which may be useful in complex separations or in two-dimensional gas chromatography separations.

Figure 9:
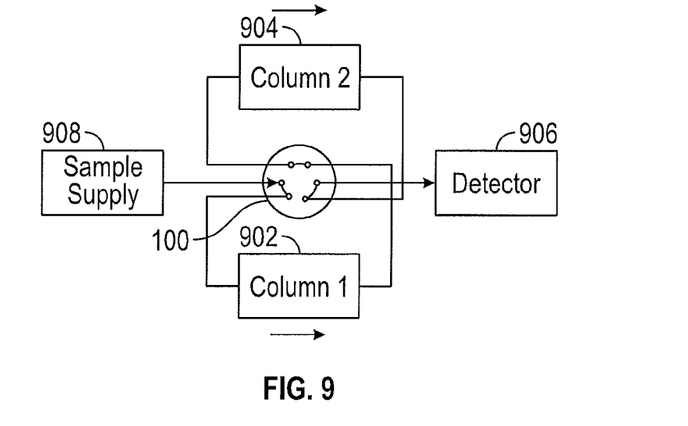
FIG. 9 is an illustration of two column recycling using the valve of the present disclosure.

Moreover, the valve 100 permits two column recycling, such as illustrated in FIG. 9 to achieve improved separation of compounds in a gas chromatography system. The ultra low internal volume and the rapid heating of the stator ports 210 to permit cycling of sample constituents, from a sample supply 908, back and forth through a first column 902 and a second column 904 multiple times, producing extremely high plate numbers and resulting in improbable separations, not possible with microfluidics or Dean's switching. Additionally, any peak broadening may be reduced, and peak capacity increased, by using negative temperature programming on the downstream column 904 connected to the detector 906.

Additionally, with its low mass, ultra-low internal volume, fast switching and high temperature limit, the valve 100 may be utilized as a comprehensive two-dimensional gas chromatography (GCxGC) modulator. As can be appreciated, the valve 100 provides better performance than a diaphragm valve, has faster switching time and longer secondary duration time that a microfluidic device, and allows use of a lower secondary flow rate and use of a microbore secondary column.

The terms and expressions which have been employed in the foregoing specification are used therein as terms of description and not of limitation, and there is no intention, in the use of such terms and expressions, of excluding equivalents of the features shown and described or portions thereof.

We claim:

1. A heated rotary valve for use in chromatography comprising
    a stator having a stator first surface and a stator second surface;
        said stator first surface having a plurality of stator connectors;
        said stator second surface including a flat plate;
        said stator having a stator port extending from each of said plurality of connectors to said flat plate of said stator second surface;
    a elongate body,
        said body having an internal bore from a body first end to a body second end,
        said stator affixed at said stator second surface to said body at said body first end,
    a rotor seal having a rotor seal first surface adjacent said stator second surface;
        said rotor seal having at least one channel in said rotor seal first surface for connection of two of said stator ports;
    a drive shaft affixed to said rotor seal,
        said drive shaft freely rotatably positioned within said internal bore of said elongate body,
        said drive shaft extending from said rotor seal to beyond said body second end,
    a element for generating heat,
        said element for generating heat affixed to one of said body at said body first end proximate said rotor seal first surface and said stator second surface and said stator, and
        wherein at least one of said rotor seal, said drive shaft, and said body is composed of a material to transmit heat from said element for generating heat to said stator.

2. The valve of claim 1 wherein said body further includes a plurality of lateral vents radially through said body from said internal bore distant said stator.

3. The valve of claim 1 wherein each of said plurality of stator connectors provides a 360 micrometer fitting.

4. The valve of claim 1 wherein said element for generating heat is an electrically-drive heating element.

5. The valve of claim 1 wherein said element for generating heat is positioned in an external groove about a body first end side surface.

6. The valve of claim 1 further comprising:
    a retaining ring about said rotor seal.

7. The valve of claim 1 further comprising:
    said stator having a stator diameter,
    said elongate body having a body diameter, and
    said body diameter less than seventy-five percent of said stator diameter.

8. An heated rotary valve system for use in chromatography comprising
    a valve including a stator, a elongate body, a rotor seal, a drive shaft, and a element for generating heat,
        said stator having a stator first surface and a stator second surface;
        said stator first surface having a plurality of stator connectors;
        said stator second surface including a flat plate;
        said stator having a stator port extending from each of said plurality of connectors to said flat plate of said stator second surface;
    a elongate body,
        said body having an internal bore from a body first end to a body second end,
        said stator affixed at said stator second surface to said body at said body first end,
    a rotor seal having a rotor seal first surface adjacent said stator second surface;
        said rotor seal having at least one channel in said rotor seal first surface for connection of two of said stator ports;
    a drive shaft affixed to said rotor seal,
        said drive shaft freely rotatably positioned within said internal bore of said elongate body,
        said drive shaft extending from said rotor seal to beyond said body second end,
    a element for generating heat,
        said element for generating heat affixed to one of said body at said body first end proximate said rotor seal first surface and said stator second surface and said stator,
        wherein at least one of said rotor seal, said drive shaft, and said body is composed of a material to transmit heat from said element for generating heat to said stator; and
    a controller,
        said controller adapted to receive a start instruction,
        said controller adapted to activate said element for generating heat upon receipt of said start instruction.

9. The valve of claim 8 wherein said body further includes a plurality of lateral vents radially through said body from said internal bore.

10. The valve system of claim 9 wherein each of said plurality of stator connectors provides a 360 micrometer fitting.

11. The valve system of claim 10 wherein said element for generating heat is an electrically-drive heating element.

12. The valve system of claim 11 wherein said element for generating heat is positioned in an external groove about a body first end side surface.

13. The valve of claim 11 further comprising:
    said stator having a stator diameter,
    said elongate body having a body diameter, and
    said body diameter less than seventy-five percent of said stator diameter.

14. A chromatography system, comprising
    a valve including a stator, a elongate body, a rotor seal, a drive shaft, and a element for generating heat,
        said stator having a stator first surface and a stator second surface;
        said stator first surface having a plurality of stator connectors;
        said stator second surface including a flat plate;
        said stator having a stator port extending from each of said plurality of connectors to said flat plate of said stator second surface;
    a elongate body,
        said body having an internal bore from a body first end to a body second end, said stator affixed at said stator second surface to said
body at said body first end,
a rotor seal having a rotor seal first surface adjacent said
stator second surface;
said rotor seal having at least one channel in said rotor
seal first surface for connection of two of said stator
ports;
a drive shaft affixed to said rotor seal,
said drive shaft freely rotatably positioned within said
internal bore of said elongate body,
said drive shaft extending from said rotor seal to
beyond said body second end,
a element for generating heat,
said element for generating heat affixed to one of said
body at said body first end proximate said rotor seal
first surface and said stator second surface and said
stator, and
wherein at least one of said rotor seal, said drive shaft,
and said body is composed of a material to transmit
heat from said element for generating heat to said
stator;
a controller,
said controller adapted to receive a oven temperature
from a temperature sensor,
said controller adapted to receive a start instruction,
said controller adapted to activate said element for generating heat upon receipt of said
start instruction for immediate heating of said stator
ports to said oven temperature;
a chromography column,
said chromatography column in communication with
said valve at a column inlet,
a sample supply,
said sample supply in communication with said valve at
a supply outlet; and
a oven,
said oven having an oven interior;
said oven having a oven wall,
said chromatography column positioned in said oven,
said sample supply positioned in said oven,
said temperature sensor positioned in said oven,
said valve positioned through said oven wall, said stator
first surface exposed to said oven interior.

15. The chromatography system of claim 14 wherein said body further includes a plurality of lateral vents radially through said body from said internal bore.

16. The chromatography system of claim 14 wherein each of said plurality of stator connectors provides a 360 micrometer fitting.

17. The chromatography system of claim 15 wherein said element for generating heat is an electrically-drive heating element.

18. The chromatography system of claim 16 wherein said element for generating heat is positioned in an external groove about a body first end side surface.

19. The valve of claim 18 further comprising:
said stator having a stator diameter,
said elongate body having a body diameter, and
said body diameter less than seventy-five percent of said stator diameter.

20. The chromatography system of claim 19, wherein
said body further includes a plurality of lateral vents radially through said body from said internal bore,
each of said plurality of stator connectors provides a 360 micrometer fitting,
said element for generating heat is an electrically-drive heating element,
said stator having a stator diameter,
said elongate body having a body diameter, and
said body diameter less than seventy-five percent of said stator diameter.

21. A chromatography system, comprising
a valve including a stator, a elongate body, a rotor seal, a drive shaft, and a element for generating heat,
said stator having a stator first surface and a stator second surface;
said stator first surface having a plurality of stator connectors;
said stator second surface including a flat plate;
said stator having a stator port extending from each of said plurality of connectors to said flat plate of said stator second surface;
a elongate body,
said body having an internal bore from a body first end to a body second end,
said stator affixed at said stator second surface to said body at said body first end,
a rotor seal having a rotor seal first surface adjacent said stator second surface;
said rotor seal having at least one channel in said rotor seal first surface for connection of two of said stator ports;
a drive shaft affixed to said rotor seal,
said drive shaft freely rotatably positioned within said internal bore of said elongate body,
said drive shaft extending from said rotor seal to beyond said body second end,
a element for generating heat,
said element for generating heat affixed to one of said body at said body first end proximate said rotor seal first surface and said stator second surface and said stator, and
wherein at least one of said rotor seal, said drive shaft, and said body is composed of a
material to transmit heat from said element for generating heat to said stator;
a controller,
said controller adapted to receive a column temperature from a chromatography column,
said controller adapted to receive a start instruction,
said controller adapted to activate said element for generating heat upon receipt of said
start instruction for immediate heating of said stator ports to said column temperature;
a chromography column including a heating system,
said chromatography column in communication with said valve at a column inlet.

* * * * *